(12) United States Patent
Eustaquio Lopes et al.

(10) Patent No.: US 12,188,854 B2
(45) Date of Patent: Jan. 7, 2025

(54) USE OF NANOFLUID TO REMOVE OIL AND SALTS FROM ROCK SAMPLES IN PETROLEUM SYSTEMS

(71) Applicant: Petróleo Brasileiro S.A.—Petrobras, Rio de Janeiro (BR)

(72) Inventors: Humberto Eustaquio Lopes, Rio de Janeiro (BR); Gerson Felizardo De Sousa Junior, Rio de Janeiro (BR); Carmen Lucia Da Silva Teixeira, Rio de Janeiro (BR); Marcia Cristina Khalil De Oliveira, Rio de Janeiro (BR)

(73) Assignee: Petróleo Brasileiro S.A.—Petrobras, Rio de Janeiro (BR)

( * ) Notice: Subject to any disclaimer, the term of this patent is extended or adjusted under 35 U.S.C. 154(b) by 132 days.

(21) Appl. No.: 17/796,540

(22) PCT Filed: Jan. 22, 2021

(86) PCT No.: PCT/BR2021/050034
§ 371 (c)(1),
(2) Date: Jul. 29, 2022

(87) PCT Pub. No.: WO2021/151183
PCT Pub. Date: Aug. 5, 2021

(65) Prior Publication Data
US 2023/0366793 A1   Nov. 16, 2023

(30) Foreign Application Priority Data
Jan. 30, 2020   (BR) ...................... 10 2020 002064 1

(51) Int. Cl.
*G01N 1/34* (2006.01)
*G01N 1/44* (2006.01)
*G01N 33/24* (2006.01)

(52) U.S. Cl.
CPC ................. *G01N 1/34* (2013.01); *G01N 1/44* (2013.01); *G01N 33/24* (2013.01)

(58) Field of Classification Search
CPC  G01N 1/34; G01N 1/44; G01N 33/24; G01N 33/241; E21B 49/00; C09K 8/035; C09K 8/58; C09K 2208/10
See application file for complete search history.

(56) References Cited

U.S. PATENT DOCUMENTS 2,617,719 A   11/1952  Stewart
4,920,792 A    5/1990  Difoggio
(Continued)

FOREIGN PATENT DOCUMENTS

BR   PI0802390 E2    3/2011
WO   2014008559 A1   1/2014
WO   2021151183 A1   8/2021

*Primary Examiner* — Alexander A Mercado
(74) *Attorney, Agent, or Firm* — Mintz, Levin, Cohn, Ferris, Glovsky and Popeo, P.C.

(57) ABSTRACT

The present invention addresses to a method of cleaning rock samples from oil systems, based on the use of a nanofluid, which is capable of considerably accelerating the process. The developed method associates the potential of oil solubilization by the nanofluid under the temporary action of an ultrasound system, being faster and more efficient than the method traditionally used by distillation, then described in the State of the Art. The used procedure reduces the time required for the removal of oil and salt, a critical step in the characterization process of rock samples, normally from 120 to 365 days, to 3 to 7 days, using a low toxicity aqueous-based nanofluid, which does not change the properties of the rocks.

4 Claims, 2 Drawing Sheets
(2 of 2 Drawing Sheet(s) Filed in Color)

(56) References Cited

U.S. PATENT DOCUMENTS

| | | |
|---|---|---|
| 8,183,182 B2 | 5/2012 | Oliveira et al. |
| 2012/0168165 A1 | 7/2012 | Holcomb et al. |
| 2014/0102480 A1 | 4/2014 | Pomerantz et al. |
| 2015/0138923 A1 | 5/2015 | Abernathy et al. |
| 2015/0247381 A1 | 9/2015 | Pursley |
| 2016/0251561 A1* | 9/2016 | Araki ............... C01G 49/08 507/103 |
| 2019/0040303 A1* | 2/2019 | Ma ................... C09K 8/584 |

* cited by examiner (a) (b)

USE OF NANOFLUID TO REMOVE OIL AND SALTS FROM ROCK SAMPLES IN PETROLEUM SYSTEMS

CROSS-REFERENCE TO RELATED APPLICATIONS

This application is a national phase application, filed under 35 U.S.C. § 371, of PCT International Patent Application No. PCT/BR2021/050034, filed Jan. 22, 2021, and claims benefit of and priority to Brazilian application BR 10 2020 002064 1, filed on Jan. 30, 2020, the disclosures of all of which are incorporated herein by reference in their entirety.

FIELD OF THE INVENTION

The present invention addresses to a method of cleaning rock samples from oil systems, based on the use of a nanofluid, which is capable of considerably accelerating the process. The developed method associates the potential of oil solubilization by the nanofluid under the temporary action of an ultrasound system, being faster and more efficient than the traditional method of extraction by distillation, to be described in the State of the Art. The used procedure reduces the time required for the complete cleaning of samples, a critical step in the characterization process of rock samples, normally from 120 to 365 days, to 3 to 7 days, using a low toxicity, water-based nanofluid that does not alter the permoporous properties of rocks.

DESCRIPTION OF THE STATE OF THE ART

In the exploratory phase of an oil well, procedures and analytical methods are applied for the characterization of samples from the oil system, aiming at studying the reservoir and identifying any problem in the steps of drilling and production of the well. (Magoon & Dow, 1994).

Particularly, the so-called rock samples consist of reservoir rocks, such as fragments, sides, cores, whole core, and their derived samples, such as cuttings and plugs. Additionally, the samples can also include source and seal-type rocks, as well as outcrops.

In the process of characterizing rock samples, specific analyses are used, such as basic and special petrophysics, sedimentological characterization, X-ray diffractometry, scanning electron microscopy, tomography, among others. To carry out these analyses, it is necessary to previously remove the oil and salts from the samples.

The traditional process of cleaning rock samples to remove the oil phase and salts, created more than 30 years ago, is carried out from extraction by distillation with organic solvents and takes about 120 days, and in some cases may extend up to 1 year. The total extraction of the oil phase and salts is essential to guarantee the quality of the subsequent analyses of these rocks, through which relevant information is obtained on the characteristics, for example, of the reservoirs.

The American Petroleum Institute (API) has a guide with best practices and recommendations for rock analysis (API 40). In particular, a section dedicated to the extraction of oil and salts. There are several methods for the removal of hydrocarbons (oil): immersion by centrifugation, extraction with a gas propelling the solvent, by liquefied gas and, the method most commonly used by most oil companies, the extraction by distillation.

The extraction by distillation is also known as Soxhlet extraction system. This system consists of a heating mantle, a volumetric flask (where the organic solvent is present), an extractor with a metal basket to store the samples, and a condenser, where cold water circulates. Each sample is placed on a filter paper with the description data. Oil removal is observed by the yellow color of the solvent, which intensifies with time. After removing the oil, the sample is subjected to extraction with another solvent to remove the salts.

Among the various solvents used, chloroform, toluene, and methanol are the most used for their solubility and boiling properties. In the distillation extraction system, the mantle heats the volumetric flask, causing the solvent to boil. The solvent vapor ascends to the condenser, and the condensed solvent comes into contact with the sample contaminated by hydrocarbons/chlorides. When the volume of sample plus solvent reaches the siphon, all the solvent is returned to the flask and the cycle is continued. Then, the samples are placed in an oven for solvent evaporation. Depending on the type of sample, the two extraction steps to remove oil and salts take from 120 to 365 days to complete.

In order to reduce the cleaning time of rock samples, an unconventional method was developed in the present invention, based on the potential for solubilization of oil and salt by a nanofluid, under the temporary action of an ultrasound system. The ultrasound system transforms electrical energy into mechanical energy. This transformation is obtained through components that promote a vibration in the frequency of 20 to 40 kHz, frequencies that are usual in an ultrasound bath. The composition of the nanofluid is already encompassed in PETROBRAS patents.

The laboratory results showed that the use of the nanofluid allows reducing from 120 to just 3 days the time required for the complete decontamination of thin section samples, without changing the physical structure or composition of the rock. This invention can be applied in cleaning samples of different types of rocks used in the world oil industry.

The State of the Art describes methods that use nanoparticles and microemulsions. Document US20120168165 discloses a method of using nanoparticles to improve the moisture of solid surfaces around the well and remove blocks of water from the well. In this document, the wetting agent and the nanoparticles are combined to produce a certain moisture content on the rock surfaces, which allows the recovery of excess water near the well (water block). Despite the use of an aqueous fluid, or a hydrocarbon with the addition of colloidal particles (nanoparticles), the aforementioned document does not address to the use of nanofluids for the removal of oils in rock samples from oil systems.

The State of the Art further defines microemulsion as a visually transparent dispersion of droplets of a liquid dispersed in a second immiscible liquid and stabilized by an interfacial film of surfactant molecules. Generally, in addition to the surfactant itself, the interfacial film consists of a co-surfactant, such as an intermediate chain alcohol or an amine. The droplet diameter of a microemulsion is of about 10 to 100 nm and its formation is independent of the mixing order of its components, but it requires a high concentration of surfactant, low interfacial tension and an adequate hydrophilic-lipophilic balance (HLB) (SHAH, 2002).

Thus, an oil-in-water microemulsion is similar to the normal micelle, where the hydrophilic part of the surfactant is oriented towards the continuous aqueous phase and the non-polar part is oriented towards the interior of the micelle.

The presence of the co-surfactant with the surfactant in the microemulsion provides flexibility to the interface in addition to reducing the interfacial tension, directing the curvature of the interface towards an energetically more favorable dispersion, thus decreasing the interfacial viscosity. As a consequence, the solubilization capacity of a microemulsion is generally much greater than that of micellar solubilization. The microemulsion intensifies the advantages of the aqueous solution of the surfactant and the pure organic solvent.

In this context, microemulsion systems with ultra-low interfacial tension and high solubilization capacity present an oil solubilization potential that is inversely proportional to the square root of the interfacial tension. Therefore, the solubilization ratio, which can be understood as the volume of the organic phase solubilized in the microemulsion divided by the volume of used surfactant, increases as the interfacial tension is reduced.

These characteristics are relevant in the widespread use and interest in microemulsions, based mainly on the high solubilization capacity of hydrophilic and hydrophobic compounds, such as oil and salts, on their large interfacial area, and on the ultra-low interfacial tension.

Microemulsions further have the advantage of requiring low energy for their formation, since this is spontaneous and their properties can be controlled by temperature and salinity. All these characteristics make microemulsions also have applications in improved oil recovery, in the extraction of organic compounds, in chemical synthesis, in the preparation of nanoparticles, and also in the solubilization of toxic compounds in order to protect the environment.

Microemulsions are used for the remediation of soils and solids contaminated by high molecular weight hydrocarbons (PI 0605007-7) and with the method for advanced oil recovery (PI 0802390-5). However, the use of microemulsions for cleaning rock samples in the laboratory prior to their characterization has not yet been disclosed by the State of the Art.

The nanofluid designated here is based on the microemulsion technology in which oil nanodrops are dispersed in water under the action of surfactant and co-surfactant compounds.

The present invention addresses to an unconventional method for accelerating the cleaning process, in the laboratory, of rock samples from oil reservoirs, based on the use of a nanofluid as a solvent, to remove oil and distilled water to remove salt, associated with an ultrasound system.

The method used in the present invention showed high performance in the removal of oil and salts from rock samples, without changing the properties of the rocks, with a significant reduction in cleaning time, a critical step in the sample characterization process, in addition to the reduction in analytical costs, and in the impact on the environment, due to the use of an aqueous-based nanofluid. It is worth to highlight that the other benefits associated with this invention are the elimination of the exposure of technicians involved in the analysis to large volumes of toxic organic solvents and the value of advance information on the characteristics of the rocks in the exploration phase of a field, contributing to the anticipation of the production decision and the financial return.

BRIEF DESCRIPTION OF THE INVENTION

The invention presents a method that combines the potential of oil solubilization by a nanofluid, under the temporary action of an ultrasound system, aiming at cleaning rock samples.

The used procedure is simple, it replaces the use of organic, toxic and high-cost solvents, leading to a reduction in the impact on the environment and the health of the technicians involved in the analyses. In addition, it considerably reduces the time to extract oil and salts from the samples, completely and in an unprecedented way altering the traditional cleaning procedure applied worldwide.

In the procedure in question, the rock sample is immersed in the nanofluid under the temporary action of an ultrasound system, for preferential removal of oil. Then, the sample is immersed in water to remove excess nanofluid and salt, also under the temporary action of ultrasound. Oil removal is clearly observed by the change in color of the nanofluid, from colorless to yellow.

The composition of the nanofluid may vary according to the type of rock. In the case of cleaning samples containing clay minerals, for example, a clay inhibitor is added to the nanofluid. The mild heating of the nanofluid (between 40 and 80° C.) also contributes to the process of removing oil from the sample.

The results obtained with the method developed in this invention showed a removal of oil and salts superior to the traditional procedure without changing the properties of the rocks; that is, it does not promote pore opening, nor does it dissolve constituent minerals of the rocks.

The results further showed a high correlation of the total porosity of a sample of reservoir rock after treatment, obtained by nuclear magnetic resonance (NMR), with the basic petrophysics data (within the margin of error), also observed in logging.

Accordingly, this invention presents a high-performance method for removing oil and salts from rock samples, with a significant reduction in cleaning time, analytical costs, impact on the health of technicians involved in the analyses and on the environment, in addition to allowing advance information on the characteristics of the rocks in the exploration phase of a field, contributing to the anticipation of the production decision and the financial return.

BRIEF DESCRIPTION OF DRAWINGS

The patent or application file contains at least one drawing executed in color. Copies of this patent or patent application publication with color drawing(s) will be provided by the Office upon request and payment of the necessary fee.

The present invention will be described in more detail below, with reference to the attached figures which, in a schematic form and not limiting the inventive scope, represent examples of its embodiment. In the drawings, there are.

DETAILED DESCRIPTION OF THE INVENTION

Figure 1:
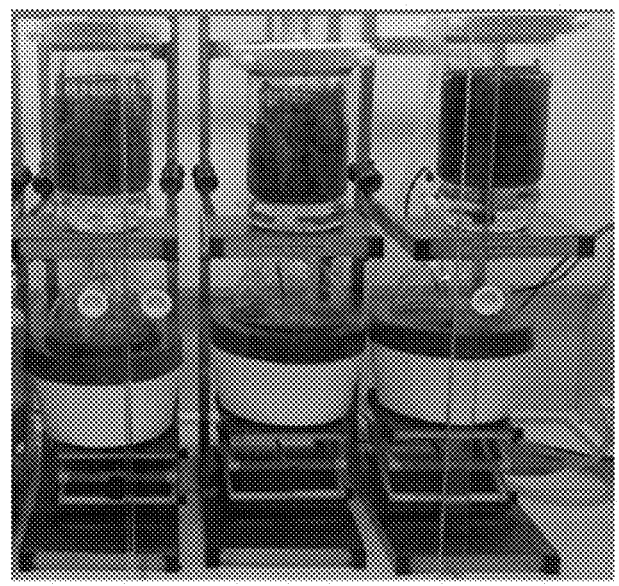
FIGS. 1 and 2, which represent the traditional system for extracting oil and salts from rock samples. This is the distillation extraction system, also known as Soxhlet extraction system, consisting of a heating mantle, a volumetric flask (where the organic solvent is present (a1)), an extractor with a metal basket to drive the samples, and a condenser, at the top, where there is circulation of cold water (b1).
Figure 2:
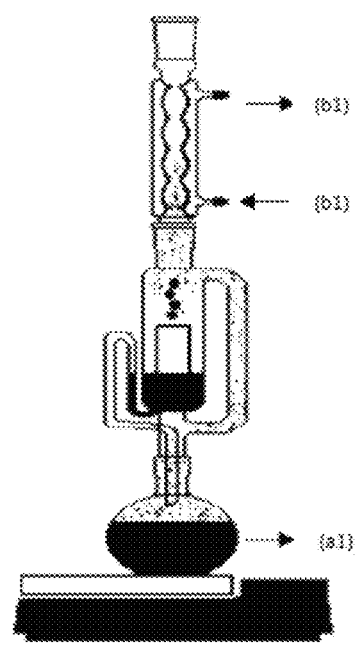

This invention presents a method that combines the potential of oil solubilization by an aqueous nanofluid, under the temporary action of an ultrasound system, aiming at cleaning rock samples from oil systems. The establishment of this new strategy for cleaning rock samples is an aspect of great importance for the world oil industry.

In this way, the present invention addresses to a method of removing hydrocarbons, particularly oil, and salts, from rock samples, comprising the following steps:
(a) adding the rock sample to a properly identified compartment;
(b) immersing the assembly from step (a) in a given volume of nanofluid at a temperature between 40 and 80° C.;
(c) subjecting the assembly immersed in step (b) to an ultrasound system, with transducers positioned on the external wall of the unit, three times, for 15 minutes each time, for two days;
(d) removing the sample from the nanofluid, immersing the same in water and submitting the same to the ultrasound system in two steps of 15 minutes each;
(e) removing excess water and sending the sample to dry in an oven;
(f) validating the efficiency of the cleaning process with specific tests. If necessary, the cleaning time can be increased.

The method of removing oil and salts from rock samples from oil systems, described in the present invention, applies to the cleaning of different types of rock samples, such as reservoir rock samples, such as fragments, cuttings, plugs of different shapes and diameters, side samples, core samples, and "whole core" samples. There can further be contemplated source and seal rocks, as well as outcrops.

With the method employed in the present invention, the time required for the complete cleaning of thin section samples and plugs is 3 and 7 days, respectively.

The experimental unit (1) of the present invention has internal compartments and two external configurations available, being represented by a glass unit (2) jacketed for the circulation of hot water, maintaining the temperature between 40 and 80° C., and a unit in stainless-steel (3) with the ultrasound transducers (4) connected through wall adapters.

The removal of oil and salts in this invention takes place without altering the permoporous properties of the rocks; that is, the extraction does not promote the opening of pores or dissolve constituent minerals of the rocks.

The method described in the invention uses a nanofluid under the temporary action of an ultrasound system for the removal of hydrocarbons (oil) and salts from rock samples of different sizes and shapes.

In this invention, the use of high performance nanofluid is disclosed to promote a pronounced reduction in the removal time of hydrocarbons and salts from rock samples.

In the present invention, a method of removing hydrocarbons and salts from rock samples by an aqueous nanofluid prepared on the basis of microemulsion technology is used.

The nanofluid used in this invention consists of 70% water, a fact that eliminates the exposure of technicians involved in the analysis to the toxicity of organic solvents used in the traditional method and, further, it can have the composition adjusted according to the characteristics of the samples.

The nanofluid in question has an average droplet size of 9.2 nm, which can vary between 5 and 90 nm, and low interfacial tension (less than 1 mN/m).

In the process described in the present invention, the rock sample is placed in a compartment and the assembly is immersed in the nanofluid at a temperature between 40 and 80° C. and maintained in this condition for two days.

In the same period of two days, the sample is submitted to the ultrasound system, with transducers positioned on the external wall of the experimental unit, three times, for 15 minutes each time.

Next, the sample is immersed in water and subjected to the ultrasound system in two 15-minute steps. Subsequently, the sample is dried in an oven.

The time required for the complete cleaning of thin section samples and plugs with the application of the method of this invention is 3 and 7 days, respectively.

The procedure of this invention is extremely simple, replaces the use of an organic solvent, toxic and expensive, and reduces the time of extraction of oil and salts from rock samples, completely and in an unprecedented way altering the traditional cleaning procedure applied worldwide.

Figure 3:
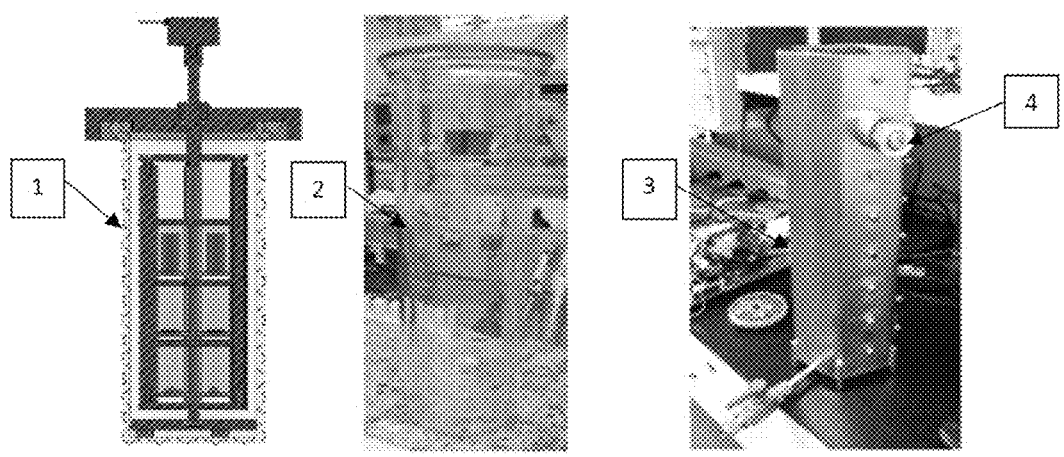
FIG. 3, which represents an experimental unit used in the method of extracting oil and salts from rock samples, described in the present invention. The experimental unit (1) has internal compartments for placing the samples individually and two possible external configurations, one in glass (2), jacketed for circulation of hot water, maintaining the temperature between 40 and 80° C., and the other in stainless-steel (3) with the ultrasound transducers (4) connected through wall adapters. There is further the possibility of placing the heating and ultrasound systems in a single stainless-steel structure. It is also possible to carry out the method in a commercial ultrasound bath, following the same described steps.
Figure 4:
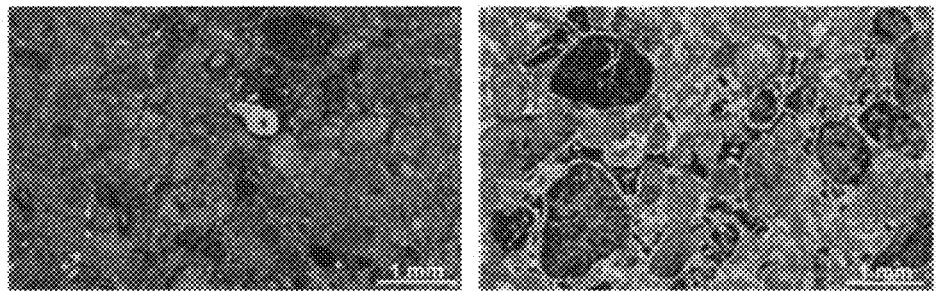
FIG. 4, which represents petrographic analysis of a sample of reservoir rock submitted to cleaning with toluene and methanol (a) with a total time of +365 days, and of the same sample submitted to cleaning with the nanofluid (b) with a total time of 3 days, object of the present invention. A cleaner/lighter appearance is observed (mainly in cement of quartz/calcite and color of the fabric grains) with the use of nanofluid.

As can be seen in FIG. 3, the experimental unit (1) has internal compartments and two external configurations available, which are a glass unit (2), jacketed for hot water circulation, in order to maintain the temperature between 40 and 80° C., and a stainless-steel unit (3) with the ultrasound transducers (4) fitted to the wall.

EXAMPLES

For the validation of the method developed in the present invention and the proof of the performance of the nanofluid, the treated samples were evaluated by mineralogical maps, petrographic evaluations and chemical analyses. The results obtained showed higher oil and salt removal than the traditional procedure and, further, without altering the properties of the rocks; that is, the method of this invention did not promote pore opening or dissolution of constituent minerals of the rocks.

The comparative analysis carried out through petrography showed that the procedure performed with the nanofluid, provided a sample of reservoir rock with a cleaner and clearer appearance, especially in the quartz/calcite cement and in the color of the fabric grains.

When a sample treated by the nanofluid of the present invention was evaluated by basic petrophysics and NMR petrophysics techniques, the results showed a high correlation of the total porosity of the sample by NMR with the basic petrophysics data, respecting the margin of error, as can be seen in Table 1.

TABLE 1

| | Basic Petrophysics × Petrophysics by NMR | | |
|---|---|---|---|
| Depth | Permeability (mD) | Porosity - PFB (Effective) | Porosity - NMR (Total) |
| 5723.30 | <0.001 | 0.56 | 1.01 |
| 5725.95 | 374 | 14.53 | 14.37 |
| 5727.35 | 228 | 15.69 | 17.14 |
| 5727.95 | 3.87 | 13.05 | 16.33 |
| 5731.00 | 178 | 17.78 | 17.04 |
| 5731.85 | 1167 | 17.14 | 15.07 |
| 5732.15 | 765 | 13.40 | 12.66 |
| 5733.85 | 39.1 | 9.70 | 10.34 |
| 5740.75 | 0.132 | 9.27 | 8.18 |
| 5741.80 | 27.74 | 11.54 | 12.01 |
| 5743.10 | 31.8 | 11.07 | 11.50 |
| 5747.40 | 153.7 | 13.62 | 12.18 |
| 5751.15 | 0.027 | 5.67 | 6.75 |
| 5752.30 | <0.001 | 4.44 | 5.90 |
| 5753.25 | <0.001 | 4.92 | 6.00 |
| 5754.30 | 5.27 | 12.12 | 12.30 |
| 5755.00 | 0.223 | 10.19 | 10.36 |

Likewise, when samples of reservoir rocks treated by the nanofluid, were evaluated by X-ray diffractometry analysis, the diffractometry results indicated similar percentages of chemical components at close depths. Request CS-47/2014 comprises samples that have been cleaned by the Soxhlet traditional system. Request CS-93/2018, on the other hand, comprises samples cleaned with nanofluid. The results of these tests can be seen in Table 2.

TABLE 2

| | | | X-Ray Diffractometry Results | | | | | | | | | |
|---|---|---|---|---|---|---|---|---|---|---|---|---|
| Depth | Sample | Request | A + M | CAL | DCD | KFD | PLG | QTZ | DOL | CDA | MAG | PIR | ANT |
| 5,130.42 m | TEST | CS-47/2014 | 26 | 68 | — | — | — | 4 | — | — | — | 2 | — |
| 5,130.60 m | TEST | CS-93/2018 | 25 | 72 | — | — | — | 3 | — | TR | — | TR | TR |
| 5,136.15 m | TEST | CS-93/2018 | 7 | 75 | — | — | — | TR | — | 18 | — | — | — |
| 5,136.31 m | TEST | CS-47/2014 | 6 | 80 | — | — | — | 1 | 13 | — | — | — | — |
| 5,139.05 m | TEST | CS-47/2014 | 7 | 91 | — | — | — | TR | 2 | — | — | — | — |
| 5,140.40 m | TEST | CS-93/2018 | 3 | 88 | — | — | — | 1 | — | 8 | — | TR | — |

Key:
A + M = Clay minerals + phyllosilicates;
CAL = Calcite;
DCD = Dolomite/Ca-Dolomite;
KFD = K-Feldspar;
PLG = Plagioclase;
QTZ = Quartz;
DOL = Dolomite;
CDA = Ca-Dolomite/Ankerite;
MAG = Magnesite;
PIR = Pyrite;
ANT = Anatase;
TR = Trace (<1%).

From the results presented, it is possible to infer that the method described in the present invention presents high performance in the removal of oil and salts from rock samples from oil systems, with a significant reduction in cleaning time, a critical step in the process of sample characterization, in addition to the reduction in analytical costs, the impact on the health of the technicians involved in the analysis, and the impact on the environment, due to the non-use of organic solvents. Another benefit associated with this invention is related to the value of advance information about the characteristics of the rocks in the exploration phase of a field, thus contributing to the anticipation of the production decision and the financial return.

In this way, it is worth bringing to the comparative context Table 3, which presents the differences between the traditional method of extraction by distillation and the method of removing oil and salts through the use of nanofluid and temporary application of ultrasound, according to this invention.

TABLE 3

Comparison between the traditional method (extraction by distillation) and the method of removing oil and salts from rock samples from oil systems using nanofluid and ultrasound

| Parameter | Traditional | New |
|---|---|---|
| Sample preparation | Paper filter | None |
| Solvents | Toluene and methanol | Aqueous nanofluid (70%) and deionized water |
| Solvent/sample volume | 9 L/40 cuttings 9 L/10 plugs | 1 L/40 cuttings 1.750 L/10 plugs |
| Analysis time | 120 to 365 days | 3 to 7 days |
| Extraction performance | medium | high |

It should be noted that, although the present invention has been described and exemplified with the attached drawings, it may undergo modifications and adaptations by technicians skilled on the subject, depending on the specific situation, but provided that within the inventive scope defined herein.

The invention claimed is:

1. A method of removal of hydrocarbons and salts from rock samples, the method comprising:
    adding a rock sample to a compartment;
    immersing the compartment in a nanofluid at a temperature between 4° and 80° C.;
    subjecting the compartment, after being immersed, to an ultrasound system with transducers positioned external of the compartment, three times, for 15 minutes each, for two days to remove hydrocarbons;
    removing the nanofluid and salt by immersing the rock sample in water and submitting the rock sample to the ultrasound system for 15 minutes, repeating twice; and
    drying the sample in an oven after twice repeating the previous step.

2. The method according to claim 1, wherein the rock sample comprises section samples and plugs, the method further comprising cleaning of section samples and plugs for a duration of 3 and 7 days, respectively.

3. The method according to claim 1, wherein the compartment is within an experimental unit having two external configurations.

4. The method according to claim 1, wherein the method takes place in a single unit comprising a heating system and an ultrasound system.

* * * * *